(12) United States Patent
Makower et al.

(10) Patent No.: US 6,638,293 B1
(45) Date of Patent: Oct. 28, 2003

(54) METHODS AND APPARATUS FOR BLOCKING FLOW THROUGH BLOOD VESSELS

(75) Inventors: Joshua Makower, Los Altos, CA (US); J. Christopher Flaherty, Los Altos, CA (US); Timothy R. Machold, Moss Beach, CA (US); Jason B. Whitt, San Francisco, CA (US); Philip C. Evard, Palo Alto, CA (US); Patrick E. Macaulay, San Jose, CA (US); John T. Garibotto, Palo Alto, CA (US); Marc Jensen, Los Gatos, CA (US)

(73) Assignee: TransVascular, Inc., Menlo Park, CA (US)

( * ) Notice: Subject to any disclaimer, the term of this patent is extended or adjusted under 35 U.S.C. 154(b) by 0 days.

(21) Appl. No.: 09/117,516
(22) PCT Filed: Jan. 31, 1997
(86) PCT No.: PCT/US97/01463
§ 371 (c)(1), (2), (4) Date: Jan. 29, 1998
(87) PCT Pub. No.: WO97/27893
PCT Pub. Date: Aug. 7, 1997

Related U.S. Application Data

(63) Continuation-in-part of application No. 08/730,327, filed on Oct. 11, 1996, now Pat. No. 6,190,353, and a continuation-in-part of application No. 08/730,496, filed on Oct. 11, 1996, now Pat. No. 5,830,222.
(60) Provisional application No. 60/010,614, filed on Feb. 2, 1996.
(51) Int. Cl.⁷ .............................................. A61M 29/00
(52) U.S. Cl. ...................................................... 606/200
(58) Field of Search ........................... 606/1, 108, 191, 606/194, 195, 200, 113, 114, 127

(56) References Cited

U.S. PATENT DOCUMENTS 3,952,747 A * 4/1976 Kimmell, Jr. ............... 606/200
4,085,757 A * 4/1978 Pevsner ....................... 606/195

(List continued on next page.)

FOREIGN PATENT DOCUMENTS

| EP | 556564 | 1/1993 |
|---|---|---|
| EP | 609386 | 8/1994 |
| EP | 707830 | 10/1995 |
| EP | 739605 | 4/1996 |
| EP | 739606 | 4/1996 |

(List continued on next page.)

OTHER PUBLICATIONS

Noriyuki Kato, Charles Semba, Michael Dake; Use of a self–expanding vascular occluder for embolization during endovascular aortic aneurysm repair; Jan.–Feb. 1997;27–23pp.

Michael Marin, Frank Veith; Endovascular repair of iliac artery and other peripheral aneurysms; 1997;194–7 & 158–9.

Primary Examiner—Kevin T. Truong
(74) Attorney, Agent, or Firm—Robert D. Buyan; Stout, Uxa, Buyan & Mullins, LLP

(57) ABSTRACT

This invention is methods and apparatus for occluding blood flow within a blood vessel (22). In a first series of embodiments, the present invention comprises a plurality of embolic devices (16) deployable through the lumen (12) of a conventional catheter (10) such that when deployed, said embolic devices (16) remain resident and occlude blood flow at a specific site within the lumen of the blood vessel (22). Such embolic devices (16) comprise either mechanical embolic devices that become embedded within or compress against the lumen of the vessel or chemical vaso occlusive agents that seal off blood flow at a given site. A second embodiment of the present invention comprises utilization of a vacuum/cauterizing device capable of sucking in the lumen of the vessel about the device to maintain the vessel in a closed condition where there is then applied a sufficient amount of energy to cause the tissue collapsed about the device to denature into a closure. In a third series of embodiments, the present invention comprises the combination of an embolization facilitator coupled with the application of an energy force to form an intraluminal closure at a specified site within a vessel.

18 Claims, 7 Drawing Sheets

U.S. PATENT DOCUMENTS

| | | | |
|---|---|---|---|
| 4,282,875 A | | 8/1981 | Serbinenko et al. |
| 4,364,392 A | | 12/1982 | Strother et al. |
| 4,402,319 A | | 9/1983 | Handa et al. |
| 4,452,785 A | | 6/1984 | Malette et al. |
| 4,551,132 A | | 11/1985 | Pasztor et al. |
| 4,580,568 A | | 4/1986 | Gianturco |
| 4,665,918 A | | 5/1987 | Garza et al. |
| 4,705,517 A | | 11/1987 | DiPisa, Jr. |
| 4,710,192 A | | 12/1987 | Liotta et al. |
| 5,035,706 A | | 7/1991 | Giantureo et al. |
| 5,104,404 A | | 4/1992 | Wolff |
| 5,152,770 A | | 10/1992 | Bengmark et al. |
| 5,167,624 A | | 12/1992 | Butler et al. |
| 5,188,616 A | | 2/1993 | Nadal |
| 5,282,824 A | | 2/1994 | Gianturco |
| 5,314,472 A | | 5/1994 | Fontaine |
| 5,342,394 A | | 8/1994 | Matsuno et al. |
| 5,354,295 A | | 10/1994 | Guglielmi et al. |
| 5,375,612 A | * | 12/1994 | Cotteneau et al. .......... 606/200 |
| 5,382,261 A | | 1/1995 | Palmaz |
| 5,456,693 A | | 10/1995 | Conston et al. |
| 5,486,193 A | | 1/1996 | Bourne et al. |
| 5,499,995 A | | 3/1996 | Teirstein |
| 5,549,635 A | | 8/1996 | Solar |
| 5,562,698 A | | 10/1996 | Parker |
| 5,575,816 A | | 11/1996 | Rudnick et al. |
| 5,578,074 A | | 11/1996 | Mirigian |
| 5,601,595 A | | 2/1997 | Smith |
| 5,601,600 A | | 2/1997 | Ton |
| 5,624,461 A | | 4/1997 | Mariant |
| 5,643,254 A | | 7/1997 | Scheldrup et al. |
| 5,643,257 A | | 7/1997 | Cohen et al. |
| 5,645,558 A | | 7/1997 | Horton |
| 5,669,931 A | | 9/1997 | Kupiecki et al. |
| 5,690,671 A | | 11/1997 | McGurk et al. |
| 5,693,067 A | * | 12/1997 | Purdy .................. 606/200 |
| 5,702,361 A | | 12/1997 | Evans et al. |
| 5,702,418 A | | 12/1997 | Ravenscroft |
| 5,702,421 A | | 12/1997 | Schneidt |
| 5,725,552 A | | 3/1998 | Kotula et al. |
| 5,733,294 A | | 3/1998 | Forber et al. |
| 5,733,325 A | | 3/1998 | Robinson et al. |
| 5,733,329 A | | 3/1998 | Wallace et al. |
| 5,746,766 A | | 5/1998 | Edoga |
| 5,755,773 A | | 5/1998 | Evans et al. |
| 5,755,779 A | | 5/1998 | Horiguchi |
| 5,766,246 A | | 6/1998 | Mulhauser et al. |
| 5,800,454 A | | 9/1998 | Jacobsen et al. |
| 5,800,457 A | * | 9/1998 | Gelbfish .................. 606/200 |
| 5,800,525 A | | 9/1998 | Bachinski et al. |
| 5,827,268 A | | 10/1998 | Laufer |

FOREIGN PATENT DOCUMENTS

| | | |
|---|---|---|
| EP | 739608 | 4/1996 |
| EP | 820726 | 7/1997 |
| JP | 9-154863 | 6/1997 |
| WO | 9412106 | 6/1994 |
| WO | 9527448 | 10/1995 |
| WO | 9600034 | 1/1996 |
| WO | 9600035 | 1/1996 |
| WO | 9601591 | 1/1996 |
| WO | 9612449 | 5/1996 |
| WO | 9612450 | 5/1996 |
| WO | 9622736 | 8/1996 |
| WO | 9636282 | 11/1996 |
| WO | 9818393 | 5/1998 |
| WO | 9823322 | 6/1998 |
| WO | 9847430 | 10/1998 |

* cited by examiner

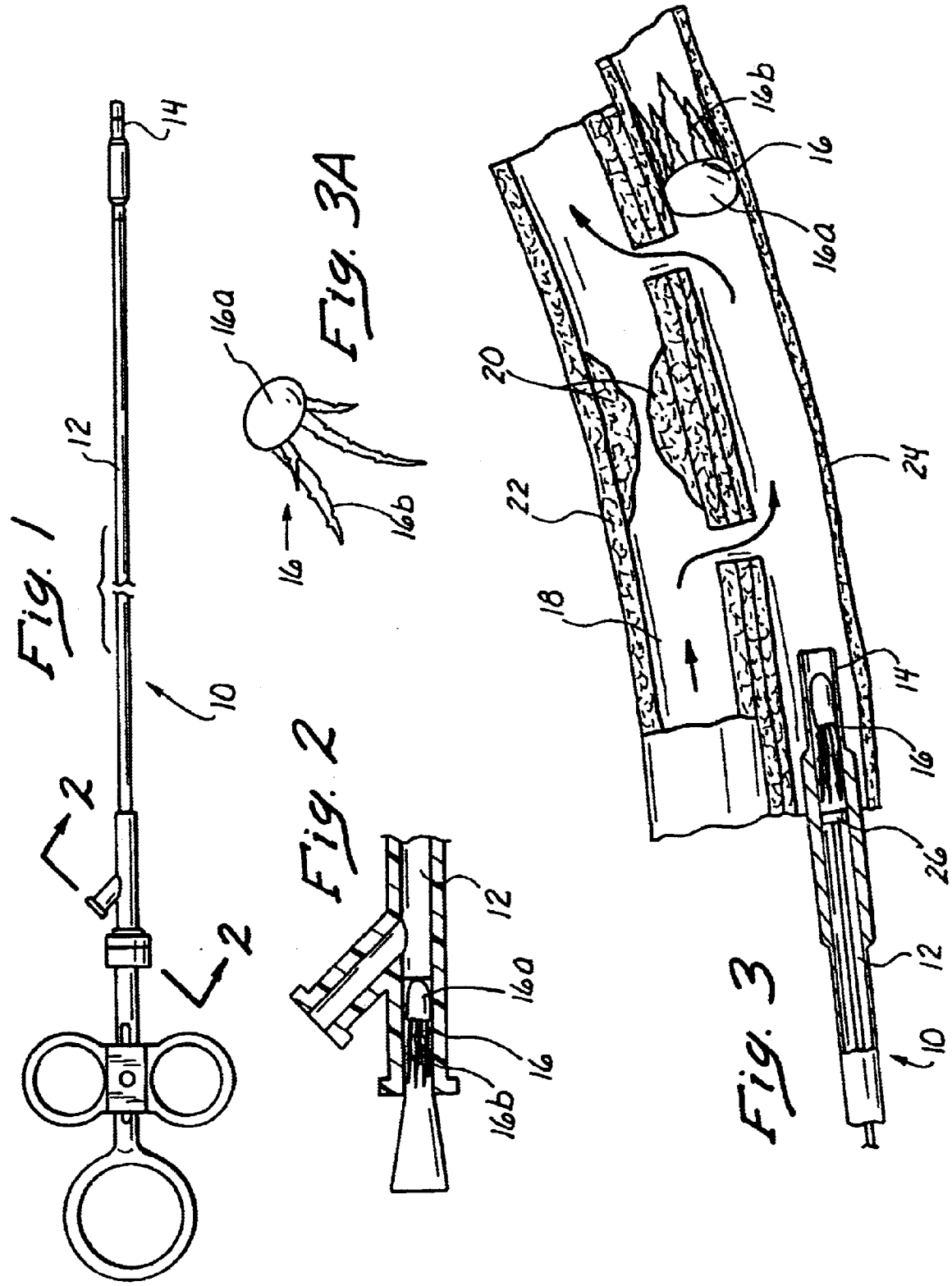

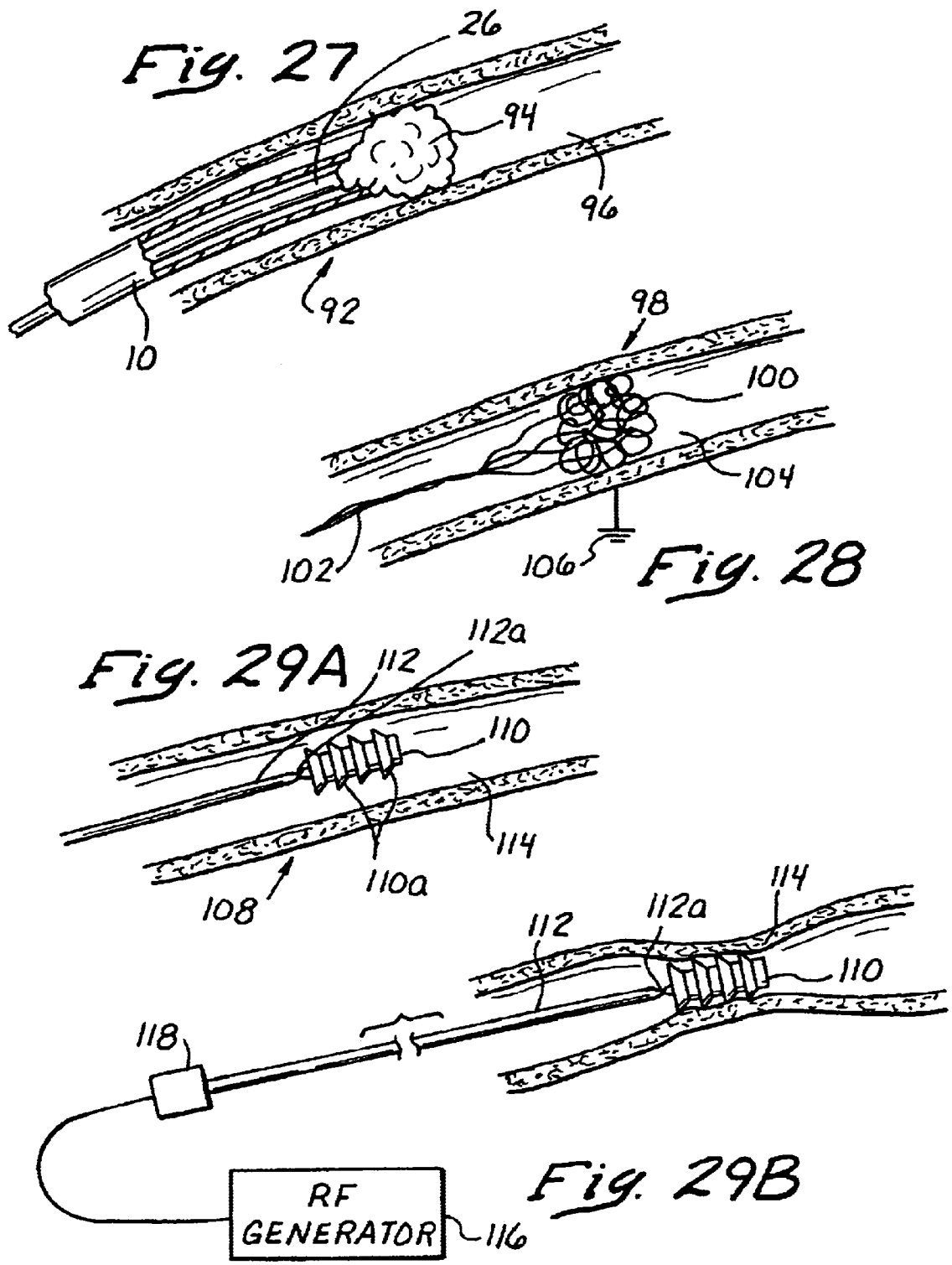

METHODS AND APPARATUS FOR BLOCKING FLOW THROUGH BLOOD VESSELS

RELATED APPLICATIONS

This patent application claims priority to U.S. Provisional Patent Application Ser. No. 60/010,614, filed on Feb. 2, 1996, and is a continuation-in-part of U.S. patent application Ser. No. 08/730,327, filed on Oct. 11, 1996 now U.S. Pat. No. 6,190,353 and Ser. No. 08/730,496, filed on Oct. 11, 1996, now U.S. Pat. No. 5,830,222, the entire disclosure of each such related application being expressly incorporated herein by reference.

FIELD OF THE INVENTION

The present invention relates generally to medical devices, and more particularly to methods and apparatus for blocking or closing the lumens of blood vessels or other anatomical conduits.

BACKGROUND OF THE INVENTION

In modern medical practice, it is often desirable to block or otherwise prevent flow through the lumen of a blood vessel or other anatomical conduit. Examples of medical procedures wherein it is desirable to block the lumens of blood vessels include: a) procedures intended to diminish or block the flow of blood into vascular aneurysms (e.g., cerebral aneurysms); b) procedures intended to occlude the side branches which emanate from a segment of a peripheral vein to prepare the vein segment for use as an in situ bypass conduit; c) procedures intended to treat varicose veins; d) transvascular, catheter-based procedures for bypassing obstructed, diseased or injured arteries as described in U.S. patent application Ser. Nos. 08/730,327 and 08/730,496; e) procedures intended to block or diminish blood flow to a tumor; f) procedures intended to close congenital or acquired arterio-venous malformations; and g) procedures intended to temporarily or permanently block blood flow through a vessel as an adjuvant to placement of an endovascular graft for treatment of an aneurysm or other therapeutic intervention.

Examples of embolization devices useable to block the lumens of some blood vessels have been described in the following U.S. Pat. No. : 5,382,260 to Dormandy, Jr. et al; U.S. Pat. No. 5,342,394 to Matsuno et al.; U.S. Pat. No. 5,108,407 to Geremia et al.; and U.S. Pat. No. 4,994,069 to Ritchart et al.; U.S. Pat. No. 5,382,261 to Palmaz; U.S. Pat. No. 5,486,193 to Bourne et al.; U.S. Pat. No. 5,499,995 to Teirstein; U.S. Pat. No. 5,578,074 to Mirigian; and also in Patent Cooperation Treaty International Publication No. WO96/00034 to Palermo.

The new transvascular catheter-based bypass procedures described in co-pending application Ser. Nos. 08/730,327 and 08/730,496 include certain coronary artery bypass procedures wherein a tissue-penetrating catheter is advanced, transluminally, into the coronary vasculature and is utilized to form at least one blood flow passageway (e.g., a puncture tract or interstitial tunnel) between an obstructed coronary artery and an adjacent coronary vein, at a site upstream of the arterial obstruction. Arterial blood will then flow from the obstructed coronary artery into the adjacent coronary vein. The lumen of the coronary vein is blocked or closed off immediately proximal to the first blood flow passageway such that arterial blood which enters the vein will be forced to flow through the vein in the retrograde direction. In this manner, the arterial blood from the obstructed artery may retroprofuse the myocardium through the coronary vein. Or, optionally, one or more secondary blood flow passageways (e.g., puncture tracts or interstitial tunnels) may be formed between the coronary vein into which the arterial blood has been shunted, and the obstructed artery or another coronary artery, to allow the arterial blood to re-enter the coronary arterial tree after having bypassed the arterial obstruction. In cases wherein such secondary blood flow passageways are formed between the coronary vein and one or more adjacent arteries, the lumen of the coronary vein may be blocked or closed off distal to such secondary passageways, to facilitate the re-entry of the shunted arterial blood into the coronary arterial circulation. These transvascular, catheter-based coronary artery bypass procedures present unique and heretofore unaddressed problems relating to the type(s) of blocking apparatus which may be utilized to block the lumen of the coronary vein proximal and/or distal to the arterial-venous blood flow passageways (e.g., puncture tracts or interstitial tunnels) formed during the procedure. In particular, when arterial blood is bypassed through a proximal segment of the Great Cardiac Vein, it will typically be desirable to block the lumen of the Great Cardiac Vein at or near its confluence from the coronary venous sinus. This proximal segment of the Great Cardiac Vein is of tapered or angular configuration and, as a result, the deployment of typical embolization coils of the type traditionally utilized to embolize or block the lumens of blood vessels or the defined spaces of aneurysm may be inappropriate, due to the fact that such embolization coils may become dislodged or work loose due to the gradually tapered or widening anatomy of-the proximal segment of the Great Cardiac Vein.

Accordingly, there exists a need in the art for the development of new methods and apparatus for blocking or otherwise sealing the lumens of blood vessels or other anatomical conduits, and which are usable in tapered (i.e., widening) segments of blood vessel (e.g., the proximal end of the great cardiac vein) and/or are capable of being removed following implantation and/or may be punctured or traversed following implantation.

SUMMARY OF THE INVENTION

The present invention provides methods and devices for blocking or closing the lumens of blood vessels to prevent blood flow therethrough. The devices of the present invention provide certain advantages over the prior art, such as i) possible removeability following implantation and/or ii) possible puncturability or retraverseability following implantation and/or iii) the ability to provide substantially immediate and permanent blockage of flow through a tapered or widening region of a blood vessel lumen (e.g., the proximal portion of the great cardiac vein).

The devices of the present invention generally fall into two main categories—i) implantable lumen-blocking devices, and ii) devices which are useable to weld or otherwise cause the lumenal walls of the blood vessel to constrict to a closed configuration or to constrict upon a member which has been placed within the blood vessel lumen.

Implantable Lumen Blocking Apparatus

The implantable lumen blocking apparatus of the present invention generally comprise i) a blood vessel engaging portion which is operative to anchor the apparatus to the surrounding wall of the blood vessel and ii) a lumen blocking portion which is operative to prevent the flow of blood in at least one direction, through the lumen of the blood vessel.

In accordance with the invention, these implantable lumen blocking apparatus are initially deployable in a radially compact configuration to facilitate their transluminal delivery through the vasculature (e.g., within a delivery catheter or other delivery tool). After reaching the desired implantation site, such lumen blocking apparatus are radially expandable to an operative configuration wherein the blood vessel engaging portion of the apparatus will engage the blood vessel wall and the lumen blocking portion of the apparatus will block the lumen of the blood vessel to prevent blood from flowing therethrough in at least one direction.

Further in accordance with the invention, the vessel-engaging portion of the apparatus may comprise a structural frame of wire or other suitable material. The lumen-blocking portion of the apparatus may comprise a membrane, sponge, fabric panel, plug, disc or other member sized to be traversely disposed within the vessel lumen to block the flow of blood.

Still further in accordance with the invention, the vessel engaging portion of the apparatus may comprise a plurality of members which emanate outwardly from a fulcrum point such that, when pressure is applied against the fulcrum point, such pressure will cause the plurality of members to become outwardly biased and thus radially expand, enlarge or exert outward pressure against the blood vessel wall, thereby deterring the apparatus from becoming dislodged or migrating from its seated position within the blood vessel.

Further in accordance with the invention, these implantable lumen-blocking apparatus may comprise radiographically visible material to permit the lumen blocking device to be visualized radiographically following implantation.

Still further in accordance with the invention, these implantable lumen-blocking apparatus may comprise resilient or shape memory material which will self-expand from its operative configuration by its own resilient force or by undergoing a phase transformation when exposed and warmed to body temperature. Alternatively, such implantable lumen blocking apparatus may comprise plastically deformable material which may be deformed from its radially compact configuration to its operative configuration by application of pressure or force. Such plastically deformable embodiments, may be initially mounted upon a delivery catheter equipped with an outward pressure exerting tool (e.g., a balloon or other mechanical means) such that, after the device has been positioned at its desired location within a blood vessel, the pressure exerting tool may be used to plastically deform the device to its radially expanded configuration wherein the engaging portion of the device will engage the vessel wall. Alternatively, some of these apparatus may be inflatable from their radially compact configuration to their operative configuration.

Still further in accordance with the invention, at least some embodiments of the implantable lumen blocking devices are removable following implantation within the lumen of a blood vessel. The means by which such removal may be effected may include a connector or other attachment, member to facilitate linkage or connection to a wire, catheter or other retraction apparatus so as to pull, retract, rescue, draw, aspirate or otherwise move the previously implanted into the lumen of the catheter or other removal vehicle to remove the apparatus from the body. Or, in embodiments wherein the vessel-engaging portion of the apparatus is formed of a shape memory alloy, the implanted apparatus may be subjectable to an in situ treatment to cause it to radially contract. Such in situ treatment may comprise the infusion of a cooled liquid (such as saline) to cause the shape memory material of the apparatus to transition from one crystalline state to another with concurrent radial contraction of the apparatus from its operative configuration to a more radially compact configuration suitable for extraction and removal.

Still further in accordance with the invention, some embodiments of the implantable lumen-blocking apparatus may incorporate a lumen-blocking portion which is retranversible (i.e. puncturable). In this manner, a needle or other puncturing element may be passed through the apparatus following its implantation to restore blood flow, or to gain access to portions of the blood vessel which are distal to the site at which the apparatus was implanted.

Still further in accordance with the invention, some embodiments of these implantable lumen-blocking apparatus may comprise a woven fabric or other tissue permeable material which will undergo cellular ingrowth or endothelialization. In these embodiments, the process of cellular ingrowth or endothelialization may be exploited to enhance the anchoring of the apparatus within the blood vessel lumen and/or to improve the long-term biocompatability of the apparatus following implantation thereof.

Lumen Welding Devices

The invention also includes apparatus for welding the lumen of a blood vessel. In accordance with these embodiments of the invention, there are provided intraluminally insertable devices having at least one suction port and at least one energy-emitting region. Suction is applied through the suction port to cause the lumen of the blood vessel to collapse in an area adjacent the energy-emitting region of the device. Thereafter, energy is delivered from the energy-emitting region to weld, cauterize or otherwise fuse the collapsed lumenal wall of the blood vessel, thereby closing the lumen of the blood vessel at that site as an alternative to the use of emitted energy, these devices may deliver an adhesive or other chemical substance capable of adhering or chemically fusing the lumen of the blood vessel to form the desired closure of the lumen.

Further in accordance with this embodiment of the invention, there is provided an intraluminally insertable device which has a balloon formed thereon, a fluid delivery port, and an energy emitting region when the balloon is inflated, the balloon will temporarily block the vessel lumen. Thereafter, a flowable conductive medium (e.g., saline solution) may be introduced through the fluid delivery port and into the vessel lumen adjacent the location of the energy emitting region. Energy is then emitted such that the energy will be transmitted through the previously introduced conductive substance, to the wall of the blood vessel, thereby resulting in shrinkage or contraction of the vessel wall so as to result in closure of the blood vessel lumen at that site.

Still further in accordance with this aspect of the invention, there are provided intraluminal devices which deploy a core or embolic member which as a diameter smaller than the lumenal diameter of the blood vessel. These devices subsequently emit radiofrequency energy or other energy to cause the wall of the blood vessel to shrink or constrict about the previously deployed core or embolic member. Thereafter, the device may be extracted, leaving the core or embolic member firmly implanted within the shrunken or constricted region of blood vessel, thereby closing the blood vessel at that site.

Further objects and advantages of the invention will become apparent to those skilled in the art upon reading and understanding of the following detailed description of the preferred embodiments, and upon consideration of the accompanying drawings wherein certain preferred embodiments and examples are shown.

BRIEF DESCRIPTION OF THE DRAWINGS

FIG. 1 is a side view of a catheter utilized to deploy certain embolic devices within the vasculature according to the present invention;

FIG. 2 is a partial cross-sectional view taken along lines 2—2 of FIG. 1;

FIG. 3 is a partial cross-sectional longitudinal view of the catheter of FIG. 1 being utilized to deploy the second of two (2) embolic devices within a respective one of two adjacently positioned blood vessels having a blood flow passageway formed therebetween via two (2) anastomotic connections;

FIG. 3a is a perspective view of a jellyfish-type embolic device according to a preferred embodiment of the present invention;

FIG. 27 is a cross-sectional view of the distal end of a catheter being utilized to deposit a mass of autologous tissue within the lumen of the blood vessel;

FIG. 28 is a cross-sectional view of a collection of conductive embolic strands deposited within the lumen of a blood vessel with an external electrical ground shown to be extending therefrom;

FIG. 29a is a cross-sectional view of a textured electrode plug positioned within the lumen of a blood vessel with an insulated conductive guidewire extending therefrom;

FIG. 29b is a cross-sectional view of the electrode plug of FIG. 29a being fused to the lumen of the blood vessel, said electrode plug being coupled to an energy source via the conductive guidewire;

DETAILED DESCRIPTION OF THE PREFERRED EMBODIMENT

Figure 4:
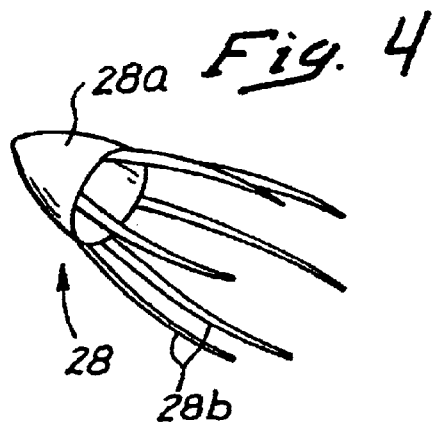
FIG. 4 is a perspective view of the jellyfish-type embolic device of FIG. 3a according to an alternative embodiment of the present invention.

Referring now to the drawings, and initially to FIGS. 1–21, there is shown methods and apparatus for occluding blood flow within a vessel at a desired location within the vasculature. The methods and apparatus disclosed herein are particularly well suited for promptly, if not immediately, occluding blood flow within a vessel having a tapered or widening lumen, such as the great cardiac vein, where vaso-occlusion is especially difficult. Likewise, the methods and apparatuses disclosed herein are ideally designed to be able to resist arterial-venous blood pressure differences and fluctuations such that blood flow may be occluded at the desired location for prolonged, if not indefinite, lengths of time.

This need to achieve vaso-occlusion especially presents itself in certain in-situ bypass procedures wherein blood flow passageways are formed between two adjacently situated blood vessels (e.g., between an obstructed coronary artery and adjacent coronary vein) to bypass a diseased, injured or obstructed segment of one blood vessel, as depicted in FIG. 3, and has been previously described in U.S. patent application Ser. Nos. 08/730,327 and 08/730,496, the teachings of which are expressly incorporated herein by reference. As shown, in order for the blood flow 18 to be rerouted around a diseased or obstructed segment 20 of vessel 22 requires that the blood flow 18 be redirected into the vessel 22 from which the flow of blood originated. To ensure that the blood flow 18 reenters the obstructed vessel 22, or to enter some other vessel after having bypassed the obstruction, it is essential that the adjacently situated blood vessel 24 through which the flow 18 is rerouted is sufficiently vaso-occluded at a site both upstream and downstream from the redirected blood flow 18.

While the prior art is replete with various embolization devices, such as helical coils, balloon catheters, and the like, such embolic devices lack features such as retrievability, retraversability and enhanced ability to remain seated within the vasculature and withstand arterial-venous blood pressure differences, particularly at points having a widening section of lumen, to thus avoid migration when deployed at the site to be embolized. In this regard, such prior art embolization devices, most notable of which being helical coils and chemical embolic agents, are typically poorly sized or adapted to maintain long term blocking at the desired widening section of lumen to be embolized as the widening lumen, coupled with the continuous non-uniform arterial-venous blood pressure exerted against the device, causes the same to migrate away from the position at which such device is deployed.

Additionally, such prior art embolic devices suffer from the drawback of being ill designed to be advanced through and deployed from the lumen of a delivery catheter. In this respect, such embolic devices must necessarily be compressed or otherwise reduced in size to be advanced through the lumen of the catheter and thereafter be capable of assuming an expanded position sufficient to occlude blood flow. Such devices, such as those described in U.S. Pat. No. 5,499,995 to Teirstein, however, either fail to achieve a sufficiently compressed state to allow for easy deployment through the lumen of a catheter or, alternatively, once deployed through the catheter fail to assume a sufficiently expanded or vaso-occlusive configuration capable of not only occluding blood flow, but remaining firmly positioned within the lumen of the vessel at the site of desired deployment.

In a first series of embodiments illustrated in FIGS. 2–21 and discussed further herein, there is shown a multiplicity of embolic devices and embolic agents that are designed and configured to be deployed at the desired site to be occluded within the vasculature using a conventional catheter 10, as shown in FIG. 1. As is well known in the art, such catheters 10 have a lumen 12 formed therein through which the embolic devices disclosed herein may be deployed at the desired site. In this regard, the embolic device 16, such as the one illustrated in FIG. 2, is loaded within the lumen 12 of the catheter and advanced therethrough via a pusher 26, more clearly shown in FIG. 3. Once the desired site to be embolized is accessed by the distal end 14 of the catheter 10, the embolic device 16 is advanced through the lumen 12 of the distal end 14 of the catheter 10 where the same remains resident.

Common to each of the embodiments disclosed herein is the advantage of each such device to either be more easily deployed, and more particularly, delivered through the lumen 12 of the catheter 10; resist dislodgment and remain more firmly positioned or seated at the desired site to be vaso-occluded; include means for retraversability to allow additional procedures to be performed therethrough at a later date; or include means to allow such devices to be retrieved, typically through a catheter, at a later date. It is further advantageous to provide such embolic devices that are radio opaque so that the position of such devices, and more particularly the placement thereof, can be determined with a high degree of accuracy. As will be recognized by those skilled in the art, such features provide the physician with enhanced capabilities to achieve greater vaso-occlusion within a patient at specific sites within the vasculature, as well as access or retrieve the same in the future, as may be necessary in later procedures.

With respect to the first of such embolic devices, there is shown in FIGS. 2, 3 and 3a a jellyfish-type embolic device 16 comprising a combination of a fabric, composite, braided, or polymer tip 16a placed over a cylindrical wire structure or frame 16b. The fabric or polymer tip 16a is preferably fabricated from a thin, stretchable material, such as either silicone, urethane, polyethylene, Teflon, nylon, Carbothane, Tecoflex, Tecothane, Tecoth, or other similar materials well-known to those skilled in the art. The fabric or polymer tip 16a may further be texturized or roughened to aid in endothelialization of the tip 16a and further, may preferably be reinforced with fabric comprised of polyester, nylon, Dacron, ePFTE, and the like, which may be molded into the cap 16a or exposed on the surface thereof. Alternatively, such reinforcement fabric may cover the entire polymer cap 16a or may be strategically located to prevent wear of such cap 16a. For example, such fabric may be utilized to stitch the cap onto the cylindrical wire structure 16b.

The cylindrical structure 16b is preferably fabricated from a malleable, radiopaque and biologically-compatible material, such as nickel titanium wire, tantalum, stainless steel, platinum, gold, tungsten, coated tungsten, titanium, MP35M Elgioy, platinum, as well as other alloys of these metals and the like, and is preferably formed to have a zig-zag configuration. The cylindrical structure 16b is further additionally formed such that the structure may exist in a first collapsed state, as depicted in FIGS. 2 and 3, for deployment through the lumen 12 of a catheter 10, and assume a second expanded position, as illustrated in FIGS. 3 and 3a, once ejected from the distal end 14 of catheter 10 at the desired point to be embolized. As will be recognized by those skilled in the art, by forming the cylindrical structure 16b from heat expansive or superelastic material, such as Nitinol, such embolic device 16 thus may assume a low profile for easier delivery through the lumen 12 of the deployment catheter 10. To further enhance the ability of the device 16 to assume such low profile, the wires comprising the cylindrical structure 16b may be formed to complimentary compress upon itself such that the diameter of the structure is greatly reduced. Likewise, such materials advantageously allow the device 16 to assume an expanded configuration which thus facilitates vaso-occlusion within the vessel 24. In this respect, the device 16 is preferably formed such that the elastic tip 16a is only formed around approximately one-half to one-third the distal end of the cylindrical portion 16b to thus allow the free end of the cylinder 16b to expand fully about the lumen of the vessel 24 once the same is deployed and allowed to assume the expanded configuration.

To further facilitate the ability of the cylindrical portion 16b to adhere to the lumen of the vessel 24 when in the expanded configuration, the cylindrical structure 16b may have bends formed thereabout to thus enhance the frictional engagement between the structure 16b and the lumen of the vessel 24. As should be recognized, to achieve the optimal vaso-occlusive effect, the embolic device 16 should be deployed such that the membrane 16a faces the head-on flow of blood 18. By facing the flow of blood 18 head-on, such blood pressure actually facilitates the ability of the device 16 to remain seated within the desired site within the lumen of the vessel 24. In this regard, the free, uncovered portion of the cylindrical structure 16b is not constricted or otherwise restrained from assuming a fully expanded configuration. In fact, as illustrated in FIG. 3a, the free ends of the cylindrical structure 16b may be configured to bow outwardly to thus embed within the wall of the lumen at the site of vaso-occlusion.

As will be recognized, the embolization device 16, when lodged within the lumen 24 of a vessel in the expanded state, is oriented such that the elastomeric fabric or polymer tip 16a produces a vaso-occlusive surface that restricts blood flow through the vessel. Advantageously, however, such fabric or polymer tip 16a further provides means for retraversibly accessing the vaso-occluded site, as may be necessary for certain procedures performed at a later time. In this respect, a catheter, for example, may be axially advanced through the drum-like occlusive barrier formed by the elastomeric tip 16a without otherwise altering the ability of the cylindrical structure 16b to remain seated axially about the lumen of the vessel. Likewise, such device 16, by virtue of the cylindrical structure 16b being fabricated from heat constrictive material, allows the device 16 to be easily retrieved through the lumen 12 of a catheter 10 by exposing the structure 16b to reduced temperatures, which thus causes the cylindrical structure 16b to assume a constricted configuration that enables the same to be axially withdrawn into the lumen 12 of a catheter 10.

Figure 5:
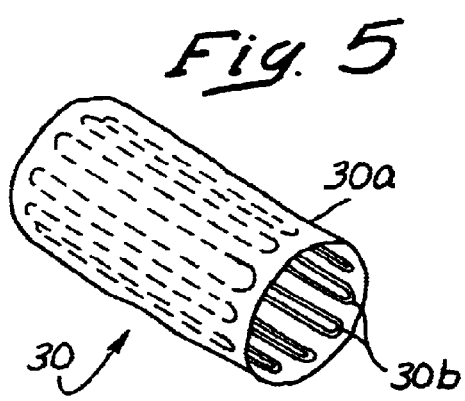
FIG. 5 is a perspective view of a sinusoidal wire-type embolic device according to the preferred embodiment of the present invention.
Figure 6:
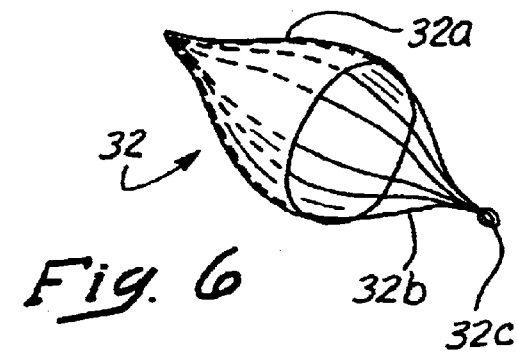
FIG. 6 is a birdcage-type embolic device according to a preferred embodiment of the present invention.

Referring to FIGS. 4, 5 and 6, there are shown alternative embodiments of the jellyfish-type embolic device according to the present invention. With respect to FIG. 4, there is shown an embolic device 28 comprised of a plurality of longitudinally extending wires 28b collectively connected at one end by a weld or an outer hypotube. The fabric or polymer tip 28a is placed about the distal one-third to one-half of the longitudinally extending wires 28b such that when deployed, the elastomeric tip 28a radially expands to form a vaso-occlusive surface. As will be recognized, the longitudinally extending wires 28b, by virtue of their arrangement, are oriented to radially embed within the lumen of the vessel and actually enhance the ability of the device 28 to become more firmly seated at the site of vaso-occlusion as greater pressure is exerted by the occluded blood flow on the fabric of polymer tip 28a. Additionally, it should be noted that such arrangement of longitudinally extending wires 28b may be easily collapsed to enable the device 28 to be retrieved through the lumen of a catheter, if necessary at a later time. To enhance such retrievability, such device may further preferably include a ring member (not shown) formed upon the weld joining the elongate wires 28b to thus provide means to hook the device and retrieve the same through the lumen of a catheter should it be necessary to remove the device and restore blood flow through the vaso-occluded vessel.

FIG. 5 depicts yet another embodiment 30 of this first class of embolic devices wherein the cylindrical structure 30b comprises round wires assuming a sinusoidal configuration. The cylindrical structure 30b as shown is entirely covered with the elastomeric tip 30a such that when deployed, the cylindrical structure 30b expands, thus causing the elastomeric tip 30a to correspondingly expand radially about the lumen of the vessel, thus inhibiting blood flow therethrough. Advantageously, by fully covering the cylindrical structure 30b with the elastomeric covering 30a, there is thus achieved a maximal blocking effect with respect to vaso-occlusion through the vessel.

Figure 5A:
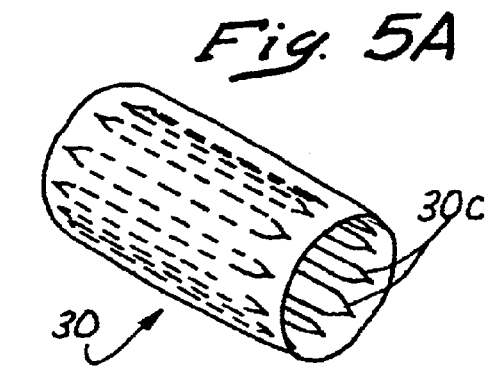
FIG. 5a is a perspective view of the sinusoidal wire-type embolic device according to an alternative preferred embodiment of the present invention.

In a preferred embodiment, the configuration of the wound wire 30b depicted in FIG. 5 may assume a zig-zag configuration 30c, as illustrated in FIG. 5a. As illustrated, the wire structure is provided with a continuous series of straight sections 30d, rigidly connected at apices to form a zig-zag structure wherein, in a compressed state, the stress is stored in the straight sections 30d of the device thereby minimizing the stress on the joints/apices and allowing for low profile delivery.

Figure 5B:
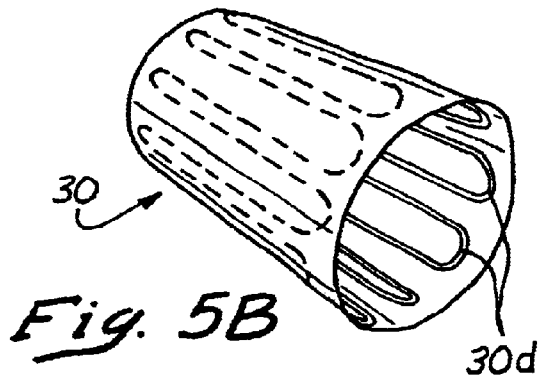
FIG. 5b is a perspective view of the sinusoidal wire-type embolic device according to an alternative preferred embodiment of the present invention.

In yet another preferred embodiment, the configuration of the wire structure 30b, 30c and pictures 5 and 5a, respectively, may be configured to form a frusto-conical structure 30d, such as that depicted in FIG. 5b. Such embodiment is deployed such that the narrow end of the device is placed in the direction of blood flow with the widening end thus being allowed to more fully expand, and thus impart a greater axial compressive force about the lumen of the vessel.

Figure 6B:
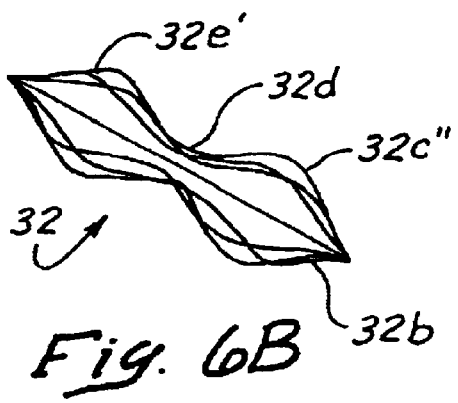
FIG. 6b is a perspective view of a preferred alternative embodiment of the birdcage-type embolic device.
Figure 6A:
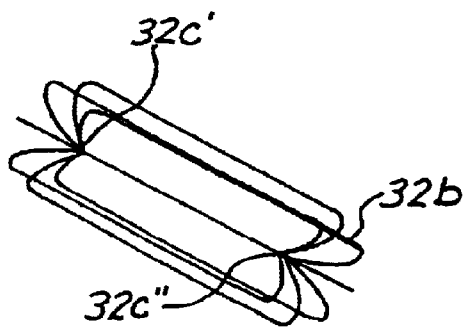
FIG. 6a is a perspective view of a preferred alternative embodiment of the birdcage-type embolic device.

Referring now to FIG. 6, there is shown an alternative birdcage-type embolization device 32 according to a preferred embodiment of the present invention. In this embodiment, the embolic device 32, comprises a multiplicity of wires running longitudinally to form a cylindrical structure 32b, connected at both ends by a weld or an outer hypotube such that the central portion of the cylinder bows outwardly to form a bulbous shape. The elastomeric tip 32a is placed about a respective end of the device 32 to thus occlude blood flow once deployed within a lumen of a vessel. In variations of this embodiment, the cylindrical portion 32b may be formed such that the ends 32c', 32c" of the structure are inverted at both ends axially within the structure, as depicted in FIG. 6a. Such configuration minimizes trauma to the vessel upon deployment and thereafter. In an alternative embodiment, as shown in FIG. 6b, the embolic device may be formed such that the center portion of the structure 32b is compressed to form a straight section 32d with bulbous structures 32e', 32e" being formed on opposed ends of the structure 32b. Advantageously, such configuration provides greater apposition to the vessel wall due to the two (2) bulbous structures 32e, 32e" making contact axially about the lumen of the vessel.

Figure 7:
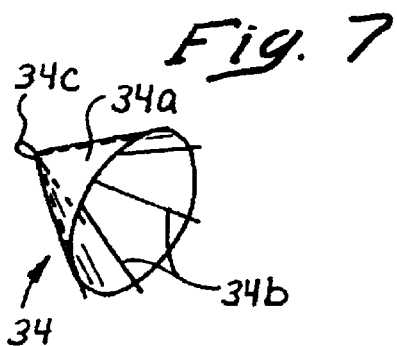
FIG. 7 is a perspective view of an umbrella-type embolic device according to a preferred embodiment of the present invention.

With respect to FIG. 7, there is shown an umbrella-type embolic 34 device according to a preferred embodiment of the present invention. The device, similar to the aforementioned jellyfish-type embolic embolizers, includes a network of longitudinally extending wires 34b surrounded by an elastic fabric or polymer cap 34a. The wires 34b according to this embodiment, however, are outwardly hinged to force such wires 34b outward to a larger diameter. As such, the device 34 easily assumes a first collapsed position where it may be advanced through the catheter for deployment, and, thereafter may expand into a second state whereby the wires spring radially outward about the lumen of the vessel. By virtue of the orientation of the embolic device 34 within the vessel, it should be recognized that the flow of blood toward the device 34 actually facilitates the ability of the device 34 to remain seated within the vessel. As an option, the device 34 may further be provided with a grab ring to enable the device to be retrieved should it become necessary at a later time to remove the same.

Figure 8:
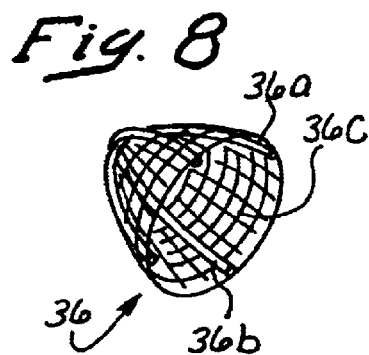
FIG. 8 is a perspective view of a cup-type embolic device according to a preferred embodiment of the present invention.

FIG. 8 depicts a cup-type embolization device 36 according to a preferred embodiment of the present invention. Such device 36 comprises at least two (2) self-expanding wire structures 36a, 36b bent at substantially their respective mid-points and intersecting at said bends to preferably form approximately a 90° angle, although other angles may be possible. The device 36 is covered with a graft or other microporous membrane 36c such that when deployed, the graft microporous membrane 36c facilitates and enhances the formation of a blood clot, thus occluding blood flow. As will be recognized, the self-expanding wire structures 36a, 36b provide substantial radial force to seat the device within the vessel. Additionally, such device 36 offers the advantages of being able to be easily compressed, to thus enabling the device to be advanced and deployed through the lumen of a catheter. Such device 36 further provides the advantage of being able to be retrieved, much like the umbrella embolic device discussed above, insofar as the intersection of the wire structures 36a, 36b provides an ideal location to hook and retrieve such device 36 through the lumen of a catheter. A catch-ring (not shown) may further be formed at the intersection of the wire structures 36a to provide simpler means for retrieving such device 36.

Figure 9A:
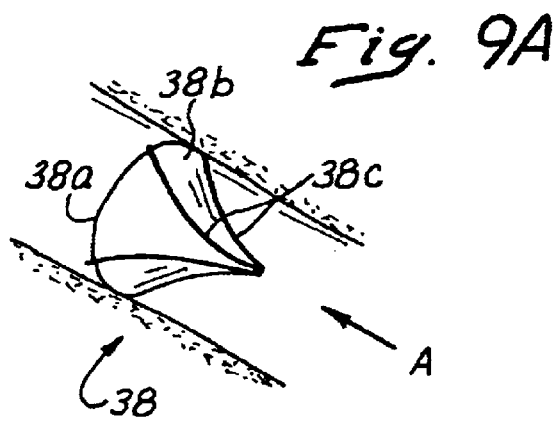
FIG. 9a is a perspective view of a traversible-type embolization device according to a preferred embodiment of the present invention, said device assuming a first closed position.
Figure 9B:
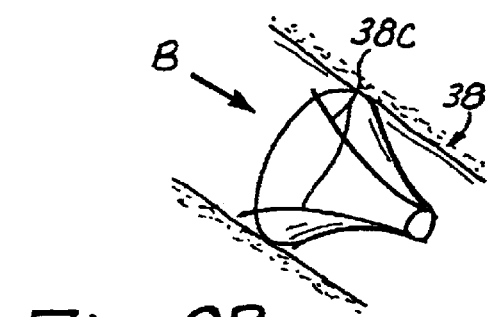
FIG. 9b is a perspective view of the traversible-type embolization device of FIG. 9a assuming a second open position.

Referring now to FIGS. 9a and 9b, there is shown a traversible embolization device 38 according to yet another preferred embodiment of the present invention. The device 38 comprises a resilient spring disc 36a forming a conical blocker 38a. The pointed end of the blocker rests in the vessel in communication with the blood flow path depicted by the letter A. To ensure that such closure is maintained, there is provided a plurality of inwardly biased members 38c that force the device 38 to assume a first closed position as depicted in FIG. 9a. Indeed, as should be recognized, the flow of blood in the direction A toward the conical shape 38a actually enhances and facilitates the ability of the device 38 to remain seated within the vessel.

Advantageously, however, the traversible embolization device 38 is capable of assuming a second open position whereby entry through the side of the device opposite the blood flow, depicted by the letter B, will cause an axial aperture to be formed within the device such that blood flow may be restored or the vessel accessed if necessary.

Figure 10:
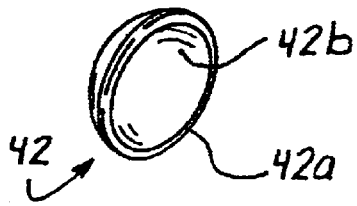
FIG. 10 is a perspective view of a diaphragm-type embolic device according to a preferred embodiment of the present invention.

Referring now to FIG. 10, there is depicted a diaphragm-type embolic device 42 according to a preferred embodiment of the present invention. Such device comprises a membrane 42b stretched over a resilient, annular outer spring 42a thus forming a disc with a flexible covering. The annular outer spring 42a may preferably be comprised of shape memory alloy, such as Nitinol, that expands when heated to certain temperatures, and more particularly, temperatures normally associated with the human body (i.e., approximately 98.6° F.). As will be recognized by those skilled in the art, the stretchable membrane 42b utilized to extend about the annular spring 42a can be penetrated and crossed, i.e., is retraversible, so that at a later time either side of the vaso-occluded site can be accessed, should it become necessary to access the same in the future.

Figure 11:
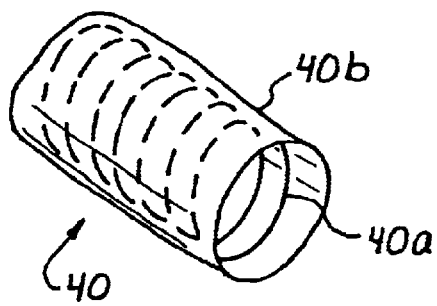
FIG. 11 is a perspective view of a capped coil-type embolic device according to a preferred embodiment of the present invention.

Referring now to FIG. 11, there is shown a cap-coil embolic device 40 according to another preferred embodiment of the present invention. Essentially, the device comprises a helical coil 40a contained within an elastomeric bag 40b. The device 40 is capable of being compressed, thus allowing the same advanced through the lumen of the deployment catheter where it is then pushed out, via the pusher, at the desired site to be occluded. Once expelled, the coil 40a expands axially within the vessel in alignment with the direction of blood flow, thus causing the elastic material 40b covering the respective ends of the coil to occlude blood flow. Such device 40, in addition to achieving the desired vaso-occlusion, has the advantage of providing a retraversible axial pathway, formed by the elastomeric material stretched over the respective ends of the device 40, that may be accessed via a catheter through the occluded site should it be necessary at some later time to perform a procedure within the vessel on the site opposite the vaso-occlusion.

Figure 12A:
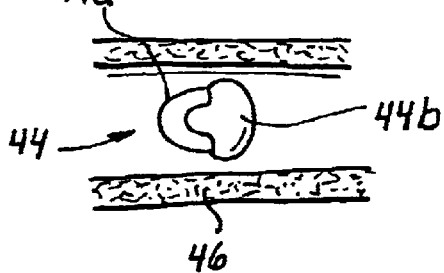
FIG. 12a is a cross-sectional view of a ring embolizer-type embolic device according to a preferred embodiment of the present invention, said ring embolizer device assuming a first uninflated state within the lumen of a blood vessel.
Figure 12B:
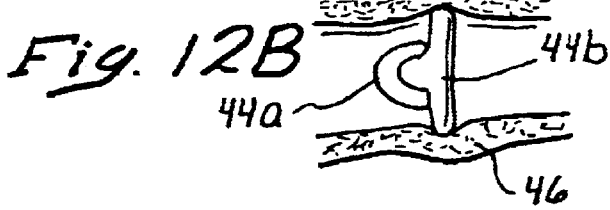
FIG. 12b is a cross-sectional view of the ring embolizer-type embolic device of 12a assuming a second inflated state within the lumen of the blood vessel.

FIGS. 12a and 12b depict a ring embolizer device 44 comprised of the combination of a first hard cap of non-distensible material 44a coupled with a second inflatable occluder 44b that is fabricated from more distensible material. The device 44 is ejected through the distal end of the catheter with the occluder 44b remaining in an uninflated state. The device is expelled from the catheter such that the occluder 44b is axially positioned within the direction of blood flow, depicted by the letter C, and is then inflated with a biologically compatible material, such as saline. By virtue of the force of the blood flow compressing against the inflated occluder 44b, the distensible material of the occluder 44b is thus caused to radially expand and flare or bite into the lumen of the vessel 46 as shown in FIG. 12b. In this respect, the occluder 44b, by virtue of it having a fixed surface area, provides radial compression about the lumen of the vessel 46 to thus cause the device 44 to remain in fixed position relative the lumen of the vessel.

Figure 13A:
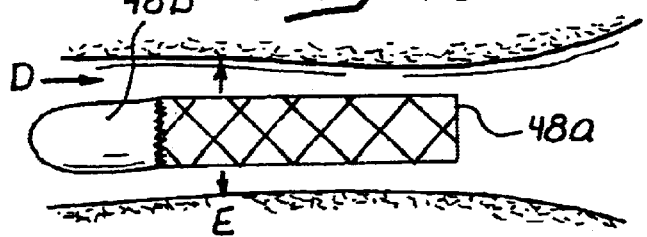
FIG. 13a is a cross-sectional view of an expanding stent/sock-type embolic device according to a preferred embodiment of the present invention, said expanding stent/sock assuming a first elongate position within the lumen of a blood vessel.
Figure 13B:
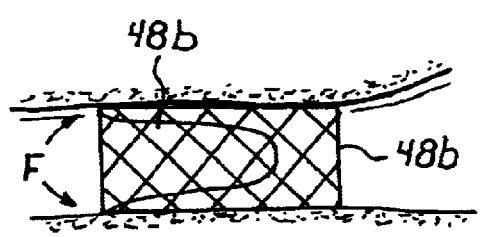
FIG. 13b is a cross-sectional view of the expanding stent/sock of FIG. 13a assuming a second inverted state causing said device to expand within said lumen.

Referring now to FIGS. 13a and 13b, there is shown an expanding stent/sock embolic device 48 according to a preferred embodiment of the present invention. The device 48 comprises a matrix 48a formed of a biologically compatible material, such as Nitinol, with a sock 48b formed at the respective end thereof. The matrix 48a is constructed such that it may assume a first collapsed position, thus enabling the device 48 to be advanced through a delivery catheter. In such collapsed state, as illustrated in FIG. 13a, the device 48 is deployed at the site to be occluded with sock 48b formed at the end of the device being expelled in the direction of the blood flow, depicted by the letter D. Blood flows through the cylindrical structure 48a and thus tends to decrease its length thereby causing a corresponding increase in its diameter, thus locking the structure 48a in place. In this regard, the matrix comprising the cylindrical structure 48a radially compresses about the lumen of the vessel, thus causing it to remain resident. As should be recognized, the cap or sock 48b is attached to the end of the cylinder to be oriented upstream the flow of blood, such that the cap or sock 48b is caused to axially invert within the cylindrical structure to thus block blood flow, as depicted by the letter F. Such design of the device 48 advantageously prevents migration from the desired site of vaso-occlusion as an increase in blood pressure pushing against such device 48 actually enhances the ability of the device 48 to become more securely seated within the vessel at the site of vaso-occlusion and further provides means for retraversing the embolic device through the sock 48b axially disposed within the matrix.

Figure 14:
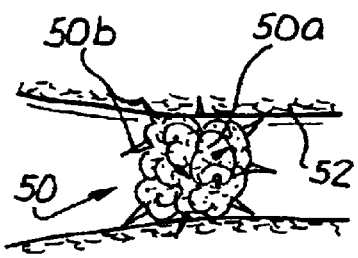
FIG. 14 is a cross-sectional view of a hook embolizer-type embolic device according to a preferred embodiment of the present invention seated within the lumen of a blood vessel.

Referring now to FIG. 14, there is shown a hook-type embolic device 50 according to the preferred embodiment of the present invention. The device 50 comprises a sponge-like structure 50a comprised of tangled wire having hooks or protrusions 50b extending radially thereabout to embed the device 50 into the vessel wall in the downstream direction of blood flow. By virtue of the frictional engagement between the hooks 50b with the lumen of the vessel 52, the device 50 is thus held in place indefinitely. The device may further preferably include radiological markers or may be radiopaque.

Figure 15:
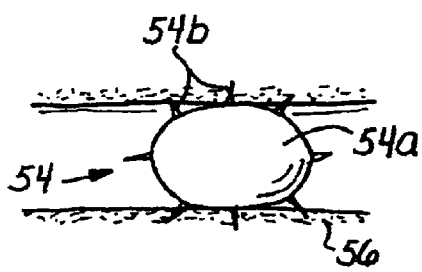
FIG. 15 is a cross-sectional view of a covered spherical coil-type embolic device according to a preferred embodiment of the present invention seated within the lumen of a blood vessel.

FIG. 15 depicts yet another further preferred embodiment of a covered spherical coil embolizer device 54 according to the present invention. Such device comprises a heat expandable coil (not shown) contained within an elastomeric covering 54a, such as silicone or polyurethane. The coil is preferably fabricated from shape memory alloy such as Nitinol, which becomes enlarged when warmed to body temperature. Essentially, the coil will expand radially at approximately 98.6° F. and will compress radially about the lumen of the vessel 56 thus causing the device to remain resident at a specific site. As will be recognized, the coil will be deployed through the catheter in a contracted state so that the device may be easily delivered to a specific site.

To further enhance the ability of the device 54 to remain resident at a specific site within the lumen of a vessel, the coil may be designed such that when heat expanded, multiple ends of the coil 54b protrude from the elastomeric covering 54a which may serve to embed the device 54 within the lumen of the vessel 56, thus enhancing its ability to remain resident.

Figure 16:
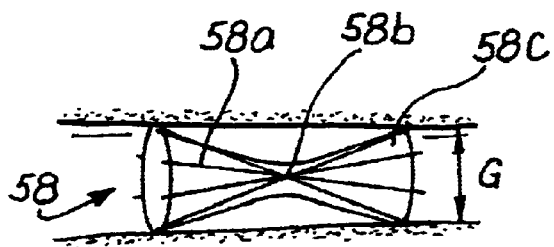
FIG. 16 is a cross-sectional view of an hourglass-type embolic device according to a preferred embodiment of the present invention seated within the lumen of a blood vessel.

Referring now to FIG. 16, there is shown an hourglass embolic device 58 according to a preferred embodiment of the present invention. The device 58 comprises a cylindrical tubular structure in which the diameter of the ends are greater than the diameter of the center of the device. Each respective end of the device is covered with a graft or other membrane 58c that, when positioned within the lumen of the vessel, occludes blood flow. The tubular structure is formed via a series of struts 58a held coupled at their mid-point 58b, thus allowing the respective ends of the struts to radially splay out which thus exerts radial pressure at both ends of the device, as depicted by the letter G. In an alternative embodiment, the struts, as opposed to being held coupled at their mid-point, are biased at their respective mid-points such that when collectively held together form the cylindrical tubular structure shown in FIG. 16.

Advantageously, by exerting radial pressure at two points along the length of the vessel, such device 58 achieves a greater ability to remain seated, and thus will not migrate from its desired site of occlusion. In this regard, such device 58 actually becomes more firmly embedded within the lumen of the vessel as greater pressure is exerted against the ends of the device 58. Furthermore, when the biased struts are utilized in the aforementioned alternative embodiment, there is additionally provided a retraversible axial pathway at the vaso-occluded site as the struts need not be coupled at their mid-point, which would otherwise obstruct such axial pathway.

Furthermore, such device 58 provides the advantage of being easily deployed, as well as retrieved, as the device 58 may easily assume a collapsed, linear configuration by lining the struts 58a in generally parallel relation to one another, thus reducing the size of the radially-extending ends of the struts of the device. Such reduction in the diameter of the ends of the device 58 allows it to be easily advanced through or withdrawn into the lumen of a catheter.

Figure 17:
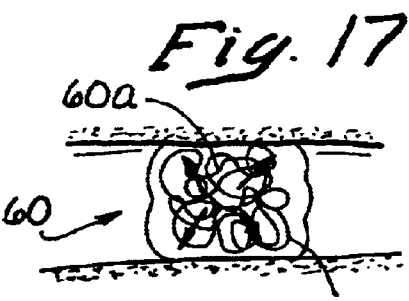
FIG. 17 is a cross-sectional view of a removable balloon-type embolic device according to a first preferred embodiment.

Referring now to FIG. 17, there is shown a removable embolic device 60, according to a preferred embodiment, comprised of an inner core 60a and an outer coating 60b, wherein the inner core 60a consists of a material that expands and contracts via controllable means, such as a chemical reacting to either heat or cold, such as contacting the device 60 with heated or chilled saline solution. Such expansion and contraction of the inner core 60a may further be controlled by the use of thermal shape memory metal, such as Nitinol, or plastic having a requisite expandable force. Such inner core 60a may further be comprised of hydrogel contained within an elastomeric bag. As will be recognized, once the inner core 60a is deployed and is reacted to assume an expanded state, the outer coating 60b expands to radially compress about the lumen of the vessel, thus occluding blood flow. As will be recognized, such device 60 advantageously allows for reversible vaso-occlusion insofar as the inner core 60a may be constricted, and thus the embolic device removed, as may be necessary at a later time to facilitate the removability of such device 60, outer coating 60b may preferably be fabricated from elastomeric materials having a smooth surface that is resistant to ingrowth and prevents blood from coagulating thereabout. As will be recognized, such features enable such device 60 to be more easily removed without the possibility of damaging or otherwise disrupting luminal tissue.

Figure 18:
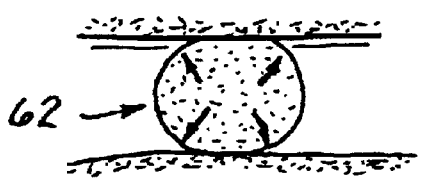
FIG. 18 is a cross-sectional view of a removable balloon-type embolic device according to a second preferred embodiment.

Similar to the embodiment depicted in FIG. 17, FIG. 18 depicts a removable balloon embolization device 62 which comprises a balloon filled with heat expandable material such that at temperatures above 90° F., the expandable material expands outwardly to hold the balloon in fixed position relative the vessel wall. By virtue of the balloon-like nature of the outer periphery of the device, there is thus provided a less traumatic means of occluding blood flow. As with the device depicted in FIG. 17, the removable balloon embolization device 62 may advantageously be retrieved by the application of a cooling source, such as cold saline. Likewise, to enhance such retrievability, the balloon embolization device 62 should be fabricated from stretchable material having a smooth outer surface that is resistant to ingrowth and prevents blood from clotting thereabout.

Figure 19:
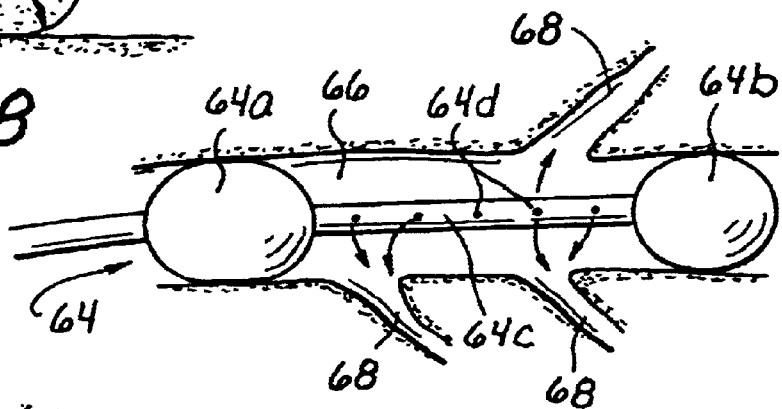
FIG. 19 is a cross-sectional view of a finder/spackler-type embolic device according to a preferred embodiment of the present invention disposed within the lumen of a blood vessel.
Figure 20:
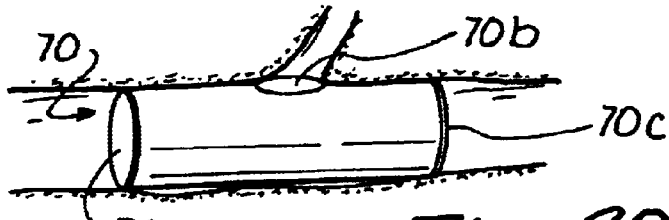
FIG. 20 is a perspective view of a three-way valve stent embolic device according to a preferred embodiment of the present invention disposed within the lumen of a blood vessel.

Referring now to FIGS. 19 and 20, and more particularly 19, there is shown two (2) embodiments of the present invention capable of restricting blood flow in more than one direction, and may further be utilized to reroute the flow of blood in a given direction. With respect to the embodiment shown in FIG. 19, there is shown an embolizer finder/spackler 64 consisting of a double balloon catheter having a central lumen, having a plurality of apertures 64d formed thereon, disposed therebetween and integrally formed therewith. When deployed as shown, each respective balloon 64a, 64b is inflated to expand about the lumen of the vessel and thus occlude blood flow therethrough. The lumen 64c disposed between the respective balloons 64a, 64b may be utilized to infuse contrast media via the apertures 64d formed thereon for defining offshoot vessels 68 extending from the portion of the occluded vessel 66. The lumen 64c disposed between the balloons may further be advantageously utilized to infuse embolization means to thus occlude any offshoot vessels 68 extending from the embolized section of vessel 66.

Such embodiment, in addition to providing the desired vaso-occlusion, further provides the advantage of defining offshoot vessels 68 that may otherwise go undetected (i.e., difficult to visualize) due to the high blood flow rate passing through the main vessel to be occluded. As will be appreciated by those skilled in the art, such high blood flow rate has a tendency to wash out or otherwise prevent sufficient contrast media from building up to detectable concentrations in such offshoot vessels. Additionally, such embodiment 64 further advantageously allows for the infusion of embolization means while such catheter remains in place in the vessel, thus eliminating the need for additional devices and procedure in the event it is necessary to occlude such offshoot vessels.

FIG. 20 depicts a three-valved stent 70 positionable within a vessel that, in addition to occluding blood flow, may be advantageously manipulated to redirect blood flow through a vessel as may be desired. In this respect, the stent 70, which may be deployed as all of the other aforementioned embodiments, namely, via expulsion through the lumen of a catheter of a desired location, is provided with three (3) valves 70a, 70b, 70c capable of occluding or facilitating blood flow. The respective valves 70a, 70b, 70c may be manipulated such that blood flow paths can be controlled at particular pressure differentials. Advantageously, such embodiment 70 may be customized to create one flow channel under one set of pressure conditions and a different flow path under different conditions.

Figure 21:
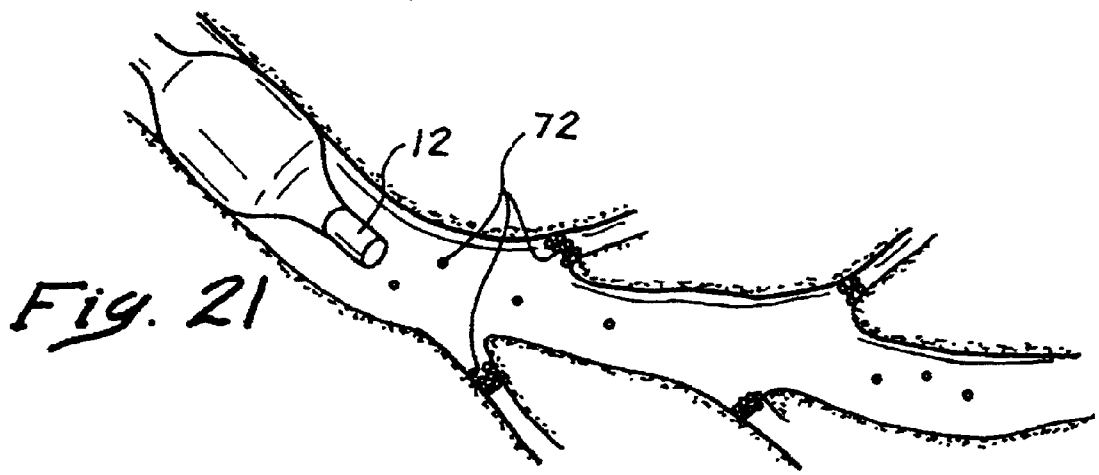
FIG. 21 is a cross-sectional view of an embolization agent being deployed within the lumen of a vessel according to a preferred embodiment of the present invention.

Referring now to FIG. 21, there is shown yet a still further preferred way to achieve the desired site-specific vaso-occlusion via the deployment of a vaso-occlusive agent 72 through the distal end of the catheter. As will be recognized, such embolic agent 72 may be an injectable fluid, such as a liquid polymer, that gels into a solid space-filling mass, at the site or sites to be occluded. Alternatively, such embolic agent 72 may comprise microspheres comprised of solid or woven material that adheres to and accumulates about the site to be occluded. Such accumulation thus causes the blood vessel to become occluded due to the generation of a blood clot about the embolic agent. To provide means for controllably releasing such embolic agent, there may be provided a vacuum source capable of applying controlled suction within the lumen 12 of the deployment catheter 10 to thus such back any excess embolic agent.

While it is understood that the aforementioned embolic devices disclosed herein are particularly well suited and adapted for vaso-occlusion within a vessel, it should further be recognized that such devices may have applicability to all cases where occlusion within a pathway is necessary.

Figure 22:
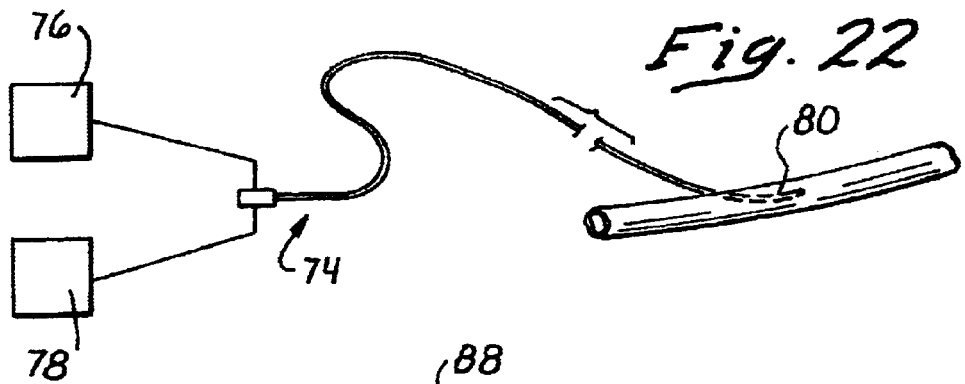
FIG. 22 is a perspective view of a system for blocking blood flow within a vessel according to a preferred embodiment of the present invention.

Referring now to FIGS. 22–26, there is shown a further methods and apparatus for occluding blood flow at a specific site within the vasculature. As illustrated in FIG. 22, the system 74 comprises the combination of a suction source 76 and an energy source 78 that are connected to and may be applied through a catheter or similar device via a hub attachment. The suction source 76 may be any of a number of devices capable of generating and sustaining a suction force. The energy source 78 may comprise either an RF or a microwave generator, laser or light source, or may just be a source of an electric current.

Figure 23:
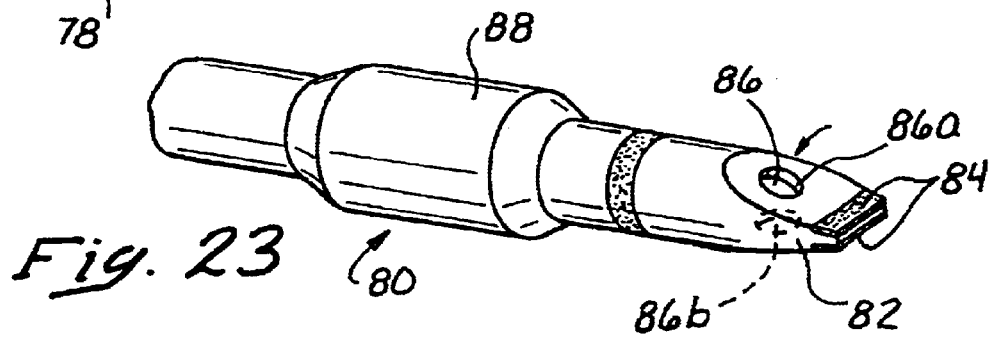
FIG. 23 is a perspective view of the distal end of a device for blocking blood flow within a vessel according to a preferred embodiment of the present invention.

Referring now to FIG. 23, there is shown a preferred embodiment of the distal end 80 of a deployment catheter utilized to occlude blood flow at a desired site according to a preferred embodiment of the system 74. As illustrated, distal end 80 comprises a distal tip 82 having at least one electrode 84 formed at the distal-most end thereof designed to impart the energy received from the energy source 78. The distal tip 82 is further provided with at least one aperture 86 through which the suction force, provided via the suction source 76, may be applied. As will be recognized, the distal end 80 preferably includes two apertures 86a, 86b formed on opposed sides of the distal tip 82 to thus provide a uniform suction thereabout. Proximal end 80 is preferably provided a balloon 88 capable of inflating radially about the delivery catheter.

Figure 24:
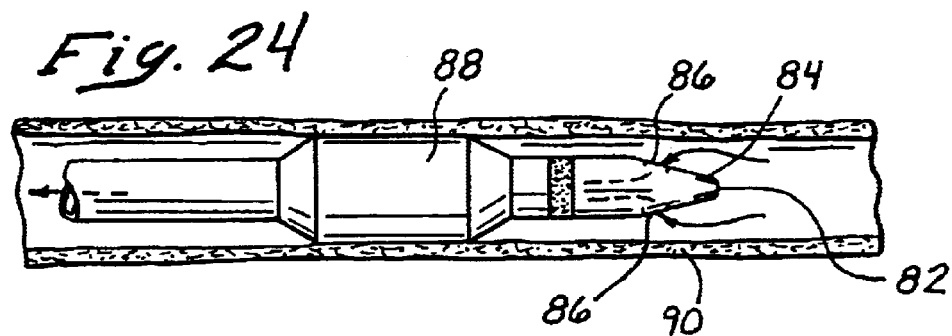
FIG. 24 is a cross-sectional view of the distal end of the device of FIG. 23 disposed within a longitudinal section of a blood vessel.
Figure 25:
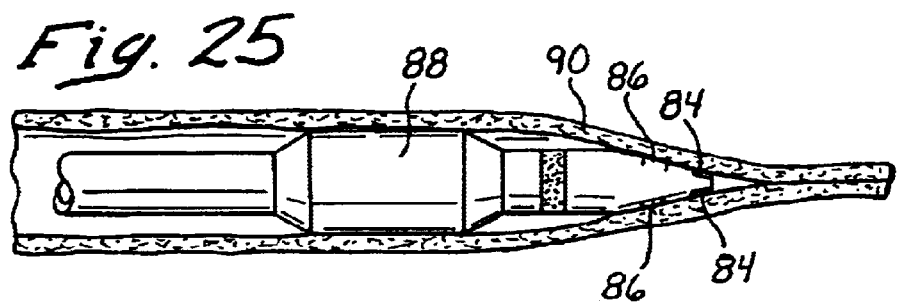
FIG. 25 is a cross-sectional view of the distal end of the device of FIG. 23 being utilized to draw in the lumen of the vessel wall about the distal tip of the device.
Figure 26:
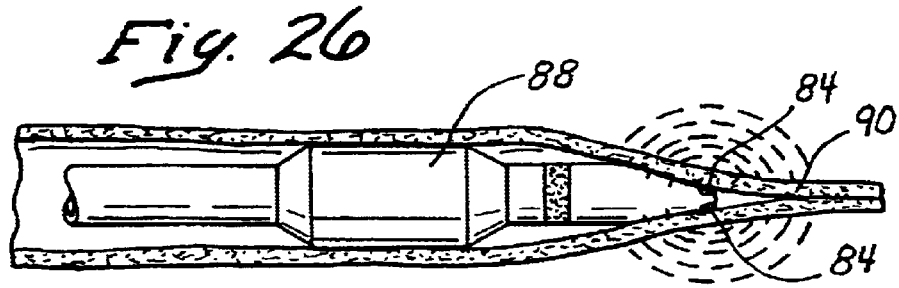
FIG. 26 is a cross-sectional view of the device of FIG. 23 being utilized to form an intraluminal closure within the blood vessel.

Referring now to FIGS. 24 through 26, there is schematically shown the steps illustrating intraluminal closure of a vessel according to application of the system 74. As shown in FIG. 24, the catheter, and more particularly distal end 80 thereof, is advanced through the vasculature to the desired site to be occluded. As discussed above, the desired site to be embolized may be accessed using conventional means known to those skilled in the art, such as by the use of a number of imaging modalities, such as by means of a specific image marker which may be disposed on distal end 80 of the catheter.

Once the desired site is accessed, the distal tip 82 of distal end 80 is positioned just proximal the site to be occluded. The balloon 88 formed proximal end 80 is then inflated to temporarily occlude blood flow, as well as to maintain the position of the distal tip 82 at the desired site where there is to be formed the intraluminal closure. Thereafter, the suction source 76 is applied such that the lumen of the vessel 90 is drawn to and collapses about the distal tip 82 of the device, as illustrated in FIG. 25. To facilitate the adherence of the lumen 90 of the vessel about the distal tip 82, such distal tip 82 may preferably be tapered. It should be recognized, however, that the lumen of the vessel may be collapsed about the distal tip of the device by mechanical means, such as by a hook extendable through the distal end of the catheter, that can embed within the lumen of the vessel and bring the same into contact with the distal end of the catheter.

While maintained in such collapsed state about the distal tip 82 of distal end 80, as illustrated in FIG. 26, the energy source 78 connected to the device may be activated to transfer energy to the electrodes 84 disposed on the distal tip 82. As illustrated, the electrodes 84 deliver the energy to the junction between the apposed collapsed vessel walls 90, thus causing the walls of the lumen 90 to become fused or otherwise denatured to form a permanent closure within the lumen of the vessel. It should be noted that to enhance the ability of the device to more thoroughly fuse or otherwise close off the lumen of the vessel, there may further be provided an energy absorbing substance applied to the lumen of the vessel 90 that denatures or otherwise becomes fused to the lumen of the vessel. Such energy absorbing substances may comprise substances such as fibrin, polymers, or collagen. Alternatively, there may be provided a conducting substance applied to or about the lumen of the vessel 90, such as saline, to thus facilitate the transfer of energy from the electrodes 84 to the lumen of the vessel 90.

As will be recognized, the intraluminal closure formed via the aforementioned two (2) step process, namely, by collapsing the tissue within the lumen of the vessel and fusing the same to form an occlusive mass, forms a permanent closure within the lumen of the vessel, such closure may nonetheless be reopened at a later time by cutting or otherwise forming a bore through the denatured tissue mass. Indeed, it is contemplated that certain channel connectors, such as those described in Applicant's co-pending PCT International Patent Application No. PCT/US97/01463, may be positioned within the fused tissue to thus provide means to restore blood flow through the vessel.

Referring now to FIGS. 27 to 30a, there is shown yet another series of embodiments of methods and apparatus for occluding blood flow within a vessel. With respect to the following class of embodiments, there is provided the combination of an embolic facilitator coupled with the application of an energy force to thus fuse the embolic facilitator to the lumen of a vessel at the specific site to be occluded. As with the first series of embolic device embodiments illustrated in FIGS. 2–21 above, the embolic facilitator is deposited within the vasculature, via a catheter, at the desired site to be embolized. Once positioned, there is applied a cauterizing or denaturing energy source which thus causes the lumen of the vessel to fuse about and fictionally adhere to the embolic device.

Referring now to FIG. 27, there is shown the first of such embodiments. The particular embodiment 92 shown comprises the use of a mass of formed autologous tissue 94 harvested from the patient, which is deposited, via a catheter, at the site to be occluded. Thereafter, a denaturing or cauterizing energy can be applied, via an electrode disposed within the lumen of the deployment catheter, the tissue 94 to thus weld the same to the lumen of the vessel 96. It should be recognized, however, that such autologous tissue 94 may alternatively be wedged into place at the desired site to be embolized without being fused to the lumen of the vessel.

Such embodiment 92 advantageously provides high biocompatability, coupled with the fact that an abundant source of such material may be readily derived from the host patient. Furthermore, the vaso-occlusion achieved by using autologous tissue has the advantage of being easily removed insofar as such tissue may be readily removed at a later time by degrading the tissue, such as by cauterizing or cutting the same, at a later date.

In an alternative embodiment, as depicted in FIG. 28, the embolic facilitator device comprises a mass of intertwined wire mesh 100, referred to herein as embolization strands, that are connected at various random points within its structure and attached to an electrode or electrodes 102 whereby such strands 100 can be sufficiently energized to cause coagulation, and hence embolization, within the lumen of the vessel. At present, it is believed that the application from 2 to 50 watts to the strands 100 is sufficient to cause the necessary coagulation at the site to be embolized. As will be understood by those skilled in the art, the application of such power necessarily requires that an external ground plate 106 be applied to thus complete the circuit utilized to deliver such power.

Referring now to FIGS. 29a and 29b, there is shown yet another embodiment of the embolization system according to the present invention. Referring firstly to FIG. 29a, there is provided a cylindrical, tubular electrode plug 110 having an insulated guidewire/conductor 112 extending from the proximal end thereof. The guidewire/conductor 112 preferably includes a breakpoint 112a formed at the distal end thereof, just proximal the electrode plug 110. As depicted in FIG. 29b, the guidewire/conductor 112 is connected, via a connector 118, to an energy source 116, which preferably comprises an RF generator.

Once the site to be occluded has been accessed, RF energy is applied via the electrode plug 110 where such energy causes the vessel 114 to shrink about the plug 110 due to dehydration and denaturation of the lumen tissue 114, as illustrated in FIG. 29b. The plug 110 thus becomes fused to the lumen 114 of the vessel and, as such, occludes blood flow. After the plug 110 has been sufficiently fused to the lumen tissue 114, the guidewire/conductor 112 is detached from the plug 110 by causing the guidewire 112 to sever at the breakpoint 112a formed on the distal end thereof. As will be recognized, the guidewire 112 may be configured to detach at the breakpoint 112a by forming the wire 112 such that the same breaks at the breakpoint 112a when sufficient tension is applied thereto. In this respect, it will be recognized that the tension necessary to break the guidewire 112 at the breakpoint 112a will be less than the tension necessary to dislodge the plug 110 from the tissue from which it is fused within the lumen of the vessel. As an alternative, the breakpoint 112a may be formed to act as a fuse which could be broken by overloading the current of energy running therethrough.

Figure 30:
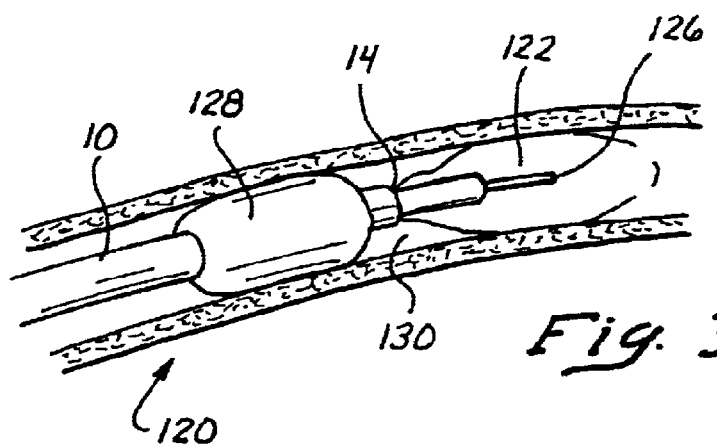
FIG. 30 is a cross-sectional view of the distal end of a catheter being utilized to infuse a conductive substance within the lumen of a blood vessel, said distal end of the catheter having an insulated electrode protruding therefrom and a balloon assuming an inflated state positioned proximal said distal end.
Figure 30A:
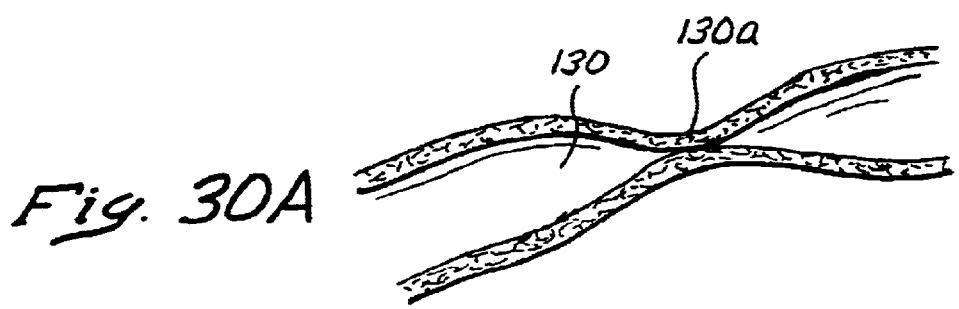
FIG. 30a is a cross-sectional view of a blood vessel having an intraluminal closure formed therein.

Referring now to FIG. 30, there is yet another preferred embodiment according to the embolization method of the present invention. In this embodiment 120, a deployment catheter 10 having an inflatable balloon 128 formed just proximal the distal end thereof is advanced to a site within the vasculature to be occluded. The balloon 128 is inflated to a point sufficient to occlude blood flow, as well as fix the distal end 14 of the catheter in position to form an intraluminal closure within the vessel at the desired site. In this regard, once maintained in the desired position, via the balloon 128, a conductive substance 122, such as saline, for example, is ejected from the distal end of the lumen of the catheter 14. A current is then passed through the conductive substance via an insulated electrode 126 extending through the distal end of the catheter 14. A current is then passed through the conductive substance 122 and about the lumen of the vessel 130, thus causing the lumen 130 to denature such that a closure 130a, as depicted in 30a, is formed. As will be recognized, deployment of the balloon 128 prior to performing such procedure is necessary insofar as the application of an electric current in the presence of blood or other protein-containing fluid causes the latter to denature and congeal, thus possibly causing an undesirable thrombogenic event within the patient.

There has thus been described in a plurality of methods and apparatus for selectively occluding blood flow at a specific site or sites within the vasculature. While it is understood that the methods and apparatus disclosed herein are particularly well suited for intraluminal closure within a blood vessel, it should be understood by persons of ordinary skill in the art that the general method and devices as described herein are equally applicable to all cases where tissue needs to be brought into apposition for the purpose of creating a bond between the tissue surfaces. Such applications of the present invention may include, but are not limited to, closing wounds, bowel, lymphatics, ducts, gaps between tissues, or punctured access sites. It should be further understood that the methods and apparatus disclosed herein may be utilized to enhance drug delivery at specific sites within the body. It is therefore understood that modifications may be made without deviating from the scope of the present invention.

What is claimed is:

1. A device which is implantable in a blood vessel to block the flow of blood in at least one direction through a lumen of that blood vessel, said device comprising:

a) a blood vessel engaging portion comprising a cylindrical frame initially disposable in a radially collapsed configuration such that said device may be passed into the lumen of said blood vessel, and subsequently expandable to an operative configuration wherein the cylindrical frame will frictionally engage a wall of the blood vessel to hold the device in a substantially fixed position within said blood vessel lumen, a hollow channel extending longitudinally through the cylindrical frame when the cylindrical frame is expanded to its operative configuration; and, b) a lumen blocking portion comprising a flexible sock member that has an open end and a substantially closed end, the open end of said flexible sock member being affixed to the cylindrical frame such that when the cylindrical frame is disposed in its operative configuration within a blood vessel, blood flowing through the blood vessel will enter the sock member and will be substantially blocked by the sock member from flowing through the hollow channel of the cylindrical frame.

2. The device of claim 1 wherein the cylindrical frame comprises a wire matrix.

3. The device of claim 1 wherein said blood vessel engaging portion further comprises an inflatable member.

4. The device of claim 1 wherein said blood vessel engaging portion has projections which embed in the wall of the blood vessel.

5. The device of claim 1 wherein said blood vessel engaging portion has hooks which embed in the blood vessel.

6. The device of claim 1 wherein said flexible sock member is a woven fabric member.

7. The device of claim 1 wherein said flexible sock member is formed at least partially of a material which is capable of being penetrated by a transluminally advanceable penetrating member, after the device has been implanted in a blood vessel lumen.

8. The device of claim 1 wherein the blood vessel engaging portion of the device is radially contractible following implantation so as to disengage from the blood vessel wall, thereby facilitating removal of the device.

9. The device of claim 8 wherein said device further comprises a connector formed on the device to facilitate connection of the device to a transluminally inserted retrieval instrument which is operative to pull the device in to an adjacent catheter.

10. The device of claim 8 wherein the cylindrical frame portion of the device is constructed such that, when the retrieval instrument is attached to the connector and a pulling force is applied to the retrieval instrument, the cylindrical frame will radially contract, thereby facilitating retraction of the device into an adjacent catheter.

11. The device of claim 1 wherein the cylindrical frame is formed at least partially of a shape memory material which transitions to said operative configuration when warmed to body temperature, but which may be radially contracted in situ by bathing the device in a cooled liquid so as to cool the device to a shape memory transition temperature which is lower than body temperature.

12. The device of claim 1 wherein the cylindrical frame is formed at least partially of resilient self-expanding material which is biased to said operative configuration such that, when unconstrained, the cylindrical frame will resiliently self-expand to said operative configuration.

13. The device of claim 1 wherein the cylindrical frame is formed at least partially of a plastically deformable material which is initially of said radially compact configuration, but which is subsequently deformable to said operative configuration by the application of pressure against said device.

14. The device of claim 1 wherein said blood vessel engaging portion comprises a radiographically visible material.

15. The device of claim 1 wherein said flexible sock member may be selectively penetrated to permit advancement of a catheter or device through the hollow channel of the cylindrical frame.

16. The device of claim 1 wherein said flexible sock member comprises a membrane.

17. The device of claim 1 wherein said membrane includes a first side formed of a first material which is resistant to cellular ingrowth, and a second side formed of a second material which is susceptible to cellular ingrowth.

18. The device of claim 1 wherein said flexible sock member is oriented on said frame relative to the direction of blood flow such that the hemodynamic pressure on said flexible member will exert force on the frame in a manner which causes the frame to exert increased outward force against the blood vessel wall.

\* \* \* \* \*